United States Patent [19]

Onda et al.

[11] 4,365,060

[45] * Dec. 21, 1982

[54] ENTEROSOLUBLE CAPSULES

[75] Inventors: Yoshiro Onda; Hiroaki Muto; Kazumasa Maruyama, all of Joetsu, Japan

[73] Assignee: Shin-Etsu Chemical Co. Ltd., Tokyo, Japan

[ * ] Notice: The portion of the term of this patent subsequent to Oct. 7, 1997, has been disclaimed.

[21] Appl. No.: 140,478

[22] Filed: Apr. 15, 1980

[30] Foreign Application Priority Data

Apr. 28, 1979 [JP] Japan .................................. 54-52914
Aug. 27, 1979 [JP] Japan ................................ 54-108888

[51] Int. Cl.$^3$ ........................ C08B 3/16; C08B 13/00
[52] U.S. Cl. ...................................... 536/65; 536/66; 424/35
[58] Field of Search .................... 106/169; 536/65, 66; 424/35

[56] References Cited

U.S. PATENT DOCUMENTS

| | | | |
|---|---|---|---|
| 2,794,799 | 6/1957 | Hiatt et al. | 260/225 |
| 2,856,399 | 10/1958 | Mench et al. | 260/224 |
| 3,493,407 | 2/1970 | Greminger | 106/189 |
| 4,017,647 | 2/1977 | Ohno | 427/3 |
| 4,138,013 | 2/1979 | Okajima | 206/528 |
| 4,226,981 | 10/1980 | Onda | 536/66 |

FOREIGN PATENT DOCUMENTS 46-29743 8/1971 Japan .................................. 424/35

Primary Examiner—Allan Lieberman
Assistant Examiner—Pat Short
Attorney, Agent, or Firm—Toren, McGeady & Stanger

[57] ABSTRACT

The invention provides a novel enterosoluble capsule for containing a medicament, which is shaped with a hitherto not used novel cellulose derivative. The cellulose derivative is a mixed ester of an alkyl-, hydroxyalkyl- or hydroxyalkyl alkylcellulose esterified with succinyl anhydride and an aliphatic monocarboxylic acid anhydride. The enterosoluble capsules have excellent enterosolubility behavior as well as sufficient pliability even without the addition of a plasticizer which is almost indispensable in the prior art materials. The cellulose derivative can be shaped into capsules not only by the conventional dipping method but also by the plastic deformation at an elevated temperature under pressure such as compression molding, vacuum forming, matchedmold forming and the like.

3 Claims, No Drawings

ENTEROSOLUBLE CAPSULES

BACKGROUND OF THE INVENTION

The present invention relates to a novel enterosoluble capsule for containing a medicament or, more particularly, to an enterosoluble capsule for containing a medicament shaped with a novel enterosoluble cellulose derivative as the base material.

An enterosoluble capsule used for oral administration of a medicament contained therein is required to be stable and undissolved in the stomach but readily dissolved when it arrives at the intestinal canals to release the medicament contained therein. In other words, the solubility of the capsule material depends on the condition of acidity or alkalinity, being insoluble in the acidic condition in the stomach but soluble in the neutral or alkaline condition in the intestinal canals. Enterosoluble capsules having such a solubility performance are conventionally made of gelatine followed by treatment with formalin to modify the solublility or followed by coating with an enterosoluble polymeric material.

One of the problems in such a gelatine-based enterosoluble capsule is the complicacy of the manufacturing process since shaping of a capsule with gelatine must be followed by the formalin treatment or by the coating procedure. Moreover, very delicate control of the process conditions is required in the formalin treatment to impart adequate enterosolubility since a gelatine capsule insufficiently treated with formalin is partly dissolved in the stomach while a gelatine capsule excessively formalin-treated becomes insoluble even in the intestinal canal.

Coating with an enterosoluble polymeric material is also not free from problems of incomplete adhesive bonding between the gelatine surface and the coating film or denaturation of the coating film by the influence of the moisture contained in the gelatine resulting in inferior enterosolubility performance.

On the other hand, there have been proposed enterosoluble capsules shaped with an inherently enterosoluble polymeric material as the base, i.e. a polymeric material which itself is insoluble in the gastric juice but soluble in the intestinal juice. Known examples of such an enterosoluble polymeric material include copolymers of aliphatically unsaturated carboxylic acids such as copolymers of methacrylic acid and methyl methacrylate and certain kinds of cellulose derivatives such as cellulose acetate phthalate, hydroxypropyl methylcellulose phthalate, methylcellulose phthalate, cellulose acetate succinate and the like.

In the shaped articles, e.g. capsules, made of the above mentioned copolymers of aliphatically unsaturated carboxylic acids, hydroxypropyl methylcellulose phthalate or methylcellulose phthalate, it is necessary to formulate a considerable amount of a plasticizer in order to improve the hardness and brittleness of the articles so that disadvantages are sometimes unavoidable by the bleeding of the plasticizer on to the surface of the shaped article which may adversely influence the effective ingredient of the medicament contained in the capsule.

Further, cellulose acetate phthalate, cellulose acetate succinate and the like shaped into a capsule are subject to a very undesirable phenomenon that they are hydrolyzed by the influence of the atmospheric moisture in the lapse of time during storage to liberate acid decomposition products such as acetic acid, phthalic acid and succinic acid resulting in gradual decrease of the solubility in the intestinal juice.

SUMMARY OF THE INVENTION

It is therefore an object of the present invention to provide a novel and improved enterosoluble capsule for medicament free from the above described problems in the prior art enterosoluble capsules.

Thus, the enterosoluble capsules of the invention are shaped with an enterosoluble cellulose derivative of a specific type as the base material which exhibits excellent enterosolubility performance, is intoxic to the human body, is stable in storage conditions not producing any noxious substances in the lapse of time capable of giving a physically and chemically stable enterosoluble capsule having excellent pliability even without the addition of a plasticizer.

The enterosoluble capsule of the invention for containing a medicament is shaped with a mixed ester of a cellulose ether substituted with alkyl groups and/or hydroxyalkyl groups esterified with acidic succinyl groups and aliphatic monovalent acyl groups.

The invention further relates to a method for the preparation of the enterosoluble capsule for medicament with the above defined cellulose derivative as the base material.

DETAILED DESCRIPTION OF THE PREFERRED EMBODIMENTS

The cellulose derivative above defined to be used for shaping the enterosoluble capsules of the invention is a novel substance newly developed by the inventors (see Japanese Patent Disclosure No. 54-61282). This material has advantages in several respects. Firstly, a very pliant film can be formed with the material with addition of no or a very small amount of plasticizers. Secondly, the films formed of the material exhibit no stickiness and never adhere to each other. Thirdly, the material is chemically and physically stable so that no denaturation takes place in the lapse of time by the influence of moisture during storage. Lastly, the purification procedure of the cellulose derivative after completion of the esterification reaction can be carried out without any difficulties so that a cellulose derivative of high purity is readily obtained.

The above mentioned cellulose derivative used in the invention has two kinds of ester groups. One is an acidic succinyl group expressed by the formula

and the other is an aliphatic monovalent acyl group represented by the general formula

where R is a monovalent aliphatic hydrocarbon group. The mixed ester of a cellulose ether with the above two kinds of ester groups is readily obtained by the esterification reaction of a cellulose ether with succinyl anhydride and an anhydride of an aliphatic monocarboxylic acid.

The cellulose ether as the starting material in the above mentioned esterification reaction is necessarily substituted or etherified with alkyl groups and/or hydroxyalkyl groups. Examples of the alkylcelluloses include methylcellulose, ethylcellulose and propylcellulose and examples of the hydroxyalkylcelluloses include hydroxyethylcellulose, hydroxypropylcellulose and hydroxybutyl cellulose. Cellulose ethers substituted with both alkyl groups and hydroxyalkyl groups are exemplified by hydroxyethyl methylcellulose, hydroxyethyl ethylcellulose, hydroxypropyl methylcellulose, hydroxypropyl ethylcellulose, hydroxybutyl methylcellulose and hydroxybutyl ethylcellulose. Further, cellulose ethers substituted with two kinds or more of hydroxyalkyl groups are also suitable such as hydroxyethyl hydroxypropylcellulose, hydroxyethyl hydroxybutylcellulose and hydroxyethyl hydroxypropyl methylcellulose. Among the above named cellulose ethers, most preferred are the hydroxyalkylalkylcelluloses having hydroxypropyl or hydroxybutyl groups as the hydroxyalkyl groups and methyl or ethyl groups as the alkyl groups due to their relatively high plasticity.

These cellulose ethers are not particularly limitative with respect to their molecular weight and the degree of molar substitution with the substituent groups although it is recommendable in the case of alkylcelluloses and hydroxyalkyl alkylcelluloses that the number of the alkyl groups as the substituent groups is 2.5 or smaller per glucose unit of the cellulose since larger molar substitution with alkyl groups increases difficulties in the esterification reaction with the above mentioned acid anhydrides. It is further recommendable that the molecular weight of the cellulose ether is in the range from about 5000 to 200,000 to obtain adequate plasticity and that the total number of the substituent groups is at least 1.5 per glucose unit since a cellulose ether with a degree of substitution smaller than above no longer exhibits desirable properties as a cellulose ether. These cellulose ethers are commercially available and can be used without further purification.

As the succinic anhydride and the aliphatic monocarboxylic acid anhydride to be reacted with the cellulose ether in the esterification reaction, commercially available technical grade products can be used as such. The aliphatic monocarboxylic acid anhydride suitable for the reaction is exemplified by the anhydrides of acetic acid, propionic acid, butyric acid, valeric acid, lauric acid and the like but the former four are preferred in view of their reactivity with the cellulose ether and their inexpensiveness.

The esterification reaction is undertaken by the method in which the cellulose ether is subjected to the esterification reaction with succinic anhydride and the aliphatic monocarboxylic acid anhydride in an aliphatic carboxylic acid as the reaction medium such as acetic acid, propionic acid, butyric acid and the like in the presence of an alkali metal salt of a carboxylic acid as the catalyst such as sodium acetate, potassium acetate and the like. Alternatively, the esterification reaction of the cellulose ether with succinic anhydride and the aliphatic monocarboxylic acid anhydride is carried out in a suitable organic solvent such as acetone and dimethylformamide in the presence of a basic catalyst such as pyridine and α-picoline.

The average numbers of substitution with the ester groups, i.e. acidic succinyl groups and the aliphatic monovalent acyl groups, per glucose unit are dependent on the properties required in the mixed ester product or on the type of the cellulose ether as the starting material. Generally speaking, it is desirable that the average numbers of substitution with acidic succinyl groups and the aliphatic monovalent acyl groups are at least 0.1 and 0.05, respectively, per glucose unit. A mixed ester product having the average numbers of substitution smaller than above is undesirable due to its inferior pliability and enterosolubility performance.

In the following, methods for fabricating capsules with the mixed ester of cellulose ether are described.

One of the most conventional methods for fabricating a capsule is the so-called dipping method or pin-mold method. In this method, the polymeric material is dissolved in a suitable solvent in an appropriate concentration to give a dipping solution, in which a pin-like male mold is dipped and pulled up gradually to form a viscous coating layer of the dipping solution therearound followed by drying with evaporation of the solvent and taking the dried polymer crust off the pin-mold to give a shaped article of the form of desired dimensions, if necessary, with finishing, e.g. trimming of the periphery, into a finished product.

The organic solvents suitable for the preparation of the dipping solution with the mixed ester of the cellulose ether in the invention are exemplified by methyl alcohol, ethyl alcohol, acetone, ethyl acetate, ethyleneglycol monomethyl ether, ethyleneglycol monoethyl ether and the like. These solvents may be used either singly or as a mixed solvent of two kinds or more according to need.

The concentration of the dipping solvent is not particularly limitative and should be determined with consideration of the viscosity of the solution and the desired wall thickness of the capsule products. It may be too much to say that a solution of lower concentration should be used when capsules of thin wall thickness are desired while thick-walled capsules are obtained with a viscous dipping solution of high concentration.

It is optional that the dipping solution is admixed with conventional additive ingredients such as coloring agents, flavor and taste improvers, flavorings, plasticizers and the like in limited amounts not to influence the advantages properties of the mixed ester of the cellulose ether. In particular, the addition of a plasticizer can be entirely omitted when a capsule of hard-type is desired different from conventional capsule-forming polymeric materials since the capsules formed of the mixed ester of the cellulose ether as such according to the invention have adequate pliability even without the addition of a plasticizer.

An alternative method for the fabrication of the capsules according to the invention is molding by plastic deformation of the material at an elevated temperature under pressure. This principle of molding is widely utilized in the technology of shaping of plastic articles but rarely utilized in manufacturing capsules. The molding of thermoplastic material according to this principle is carried out by compression molding, injection molding and extrusion molding of the polymeric material in the form of powder, granules, pellets and the like as well as by vacuum forming, pressure forming and matched-mold forming of a sheet prepared in advance with the polymeric material.

Advantages in the plastic deformation molding over the above described dipping method are obtained chiefly by the unnecessity of an organic solvent since the use of an organic solvent is undesirable from the standpoints of workers' health and atmospheric pollution as well as the danger of fire or explosion. Furthermore, the method of plastic deformation molding is advantageous owing to the much better productivity than in the dipping method so that the method is recommendable, especially, when the plastic material has a sufficient heat stability to withstand the temperature of molding.

The temperature of molding for shaping capsules with the mixed ester of the cellulose ether is in the range from 60° to 250° C. or, preferably, from 80° to 200° C. since plastic flow of the cellulose derivative is insufficient at a temperature below 60° C. leading to inhomogeneity of the products while thermal decomposition of the material takes place at a temperature higher than 250° C.

The molding pressure in compression molding or injection molding is at least 5 kg/cm² or, preferably, in the range from 10 to 2000 kg/cm².

It is optional that various kinds of additive ingredients are admixed to the mixed ester of the cellulose ether prior to molding including plasticizers, lubricants, antioxidants, coloring agents, flavor and taste improvers and the like.

Plasticizers are added when higher pliability is desired in the shaped articles, e.g. capsules. Suitable plasticizers are, for example, ethyleneglycol, diethyleneglycol, polyethyleneglycol, propyleneglycol, di- and tripropyleneglycols, polypropyleneglycol, glycerine and esters thereof such as mono-, di- and triacetins, esters of phthalic acid such as dimethyl phthalate and diethyl phthalate, tri-n-butyl citrate and the like.

Addition of lubricants is effective in improving the workability in molding and suitable lubricants are exemplified by stearic acid and salts and esters thereof such as magnesium stearate, calcium, stearate, n-butyl stearate and the like, ester waxes such as beeswax, carnauba wax, montanic acid esters and the like, polyethylene wax and rice wax.

In addition to the manufacturing of capsules per se by the plastic deformation method apart from the medicament to be contained therein, a method of encapsulation of a pre-shaped tablet is also applicable with a sheet of the inventive cellulose derivative prepared in advance. Thus, a tablet is sandwiched between two pieces of the film of the cellulose derivative and heat-sealed with pressure by pressing the films at the portions just outside the tablet on to the side surface of the tablet to give an enterosoluble encapsulated tablet.

Following are the examples to illustrate the procedure for the preparation of mixed esters of cellulose ethers and shaping of capsules with these mixed esters. In the examples, parts are all given by parts by weight.

EXAMPLE 1

Into a reaction vessel equipped with a stirrer were introduced 100 parts of glacial acetic acid, 20 parts of sodium acetate, 20 parts of a cellulose ether of the kind indicated in Table 1 below, indicated amount of succinyl anhydride and indicated kind and amount of an aliphatic monocarboxylic acid anhydride and the reaction mixture was heated at 85° C. for 3 hours to effect the esterification reaction.

After the end of the above reaction time, water was added to the reaction mixture to precipitate the reaction product which was washed with water and dried to give the mixed esters containing the acidic succinyl groups and the aliphatic monovalent acyl groups as shown in Table 1. The cellulose ethers used as the starting material appearing in Table 1 were as follows.

HPC: hydroxypropylcellulose, in which the average number of substitution with hydroxypropoxyl groups was 3.0 per glucose unit.

HPMC: hydroxypropyl methylcellulose, in which the average numbers of substitution with hydroxypropoxyl groups and methoxyl groups were 0.27 and 1.82, respectively, per glucose unit.

HEHPC: hydroxyethyl hydroxypropylcellulose, in which the average number of substitution with hydroxyethoxyl groups and hydroxypropoxyl groups were 2.5 and 0.32, respectively, per glucose unit.

HBMC: hydroxybutyl methylcellulose, in which the average numbers of substitution with hydroxybutoxyl groups and methoxyl groups were 0.10 and 1.80, respectively, per glucose unit.

In the next place, the above obtained Samples No. 1 to No. 6 shown in Table 1 as well as comparative Samples No. 7 and No. 8 below were examined for the stability against hydrolysis and elongation of the films formed therewith in the testing procedures given below to give the results shown in Table 2. Sample No. 7: cellulose acetate phthalate, in which the average numbers of substitution with acetyl groups and phthaloyl groups were 1.84 and 0.76, respectively, per glucose unit. Sample No. 8: hydroxypropyl methylcellulose phthalate, in which the average numbers of substitution with hydroxypropoxyl groups, methoxyl groups and phthaloyl groups were, 0.22 1.80 and 0.68, respectively, per glucose unit.

Testing Method for the Stability Against Hydrolysis (a) Determination of free aliphatic carboxylic acid: the sample kept at 60° C. in an atmosphere of 100% relative humidity for 6 days or 12 days was extracted with diethyl ether for 5 hours in a Soxhlet's extractor and the amount of the aliphatic monocarboxylic acid in the ether extract was determined by gas chromatography.

(b) Determination of free acid other than aliphatic monocarboxylic acid: the sample kept at 60° C. in an atmosphere of 100% relative humidity for 6 days or 12 days was dried at 105° C. for 2 hours and 1.5 g of weighed amount of the sample was dissolved in 50 ml of a 1:1 by volume mixed solvent of methylene chloride and methyl alcohol. The solution was admixed with 100 ml of water and then 100 ml of n-hexane as a phase separation aid and shaken vigorously. After standing and separation into layers, the aqueous layer was taken and combined with the washing water of the organic layer with 100 ml of water and the thus obtained water extract was titrated with 0.1 N aqueous solution of sodium hydroxide to determine total amount of free acids. The amount of free acid other than aliphatic monocarboxylic acid, viz. succinic acid or phthalic acid, was obtained as the difference between here obtained value and the value obtained in (a) above.

TABLE 1

| Sample No. | Reactants | | | Product | |
|---|---|---|---|---|---|
| | Cellulose ether | Succinic anhydride, parts | Aliphatic monocarboxylic acid, parts | Acidic succinyl groups, DS | Aliphatic monovalent acyl groups, DS |
| 1 | HPC | 4 | Acetic anhydride, 20 | 0.20 | 0.86 |
| 2 | HPC | 6 | Acetic anhydride, 20 | 0.35 | 0.76 |
| 3 | HPMC | 6 | Acetic anhydride, 32 | 0.25 | 0.57 |

TABLE 1-continued

| Sample No. | Reactants | | | Product | |
|---|---|---|---|---|---|
| | Cellulose ether | Succinic anhydride, parts | Aliphatic monocarboxylic acid, parts | Acidic succinyl groups, DS | Aliphatic monovalent acyl groups, DS |
| 4 | HPMC | 7 | Acetic anhydride, 15 | 0.42 | 0.40 |
| 5 | HEHPC | 6 | Propionic anhydride, 40 | 0.30 | 0.85 |
| 6 | HBMC | 6 | Propionic anhydride, 20 | 0.30 | 0.60 |

DS: degree of substitution with the substituent groups per glucose unit

TABLE 2

| Sample No. | Stability against hydrolysis | | | | Elongation of film, % |
|---|---|---|---|---|---|
| | After 6 days | | After 12 days | | |
| | *1 | *2 | *1 | *2 | |
| 1 | 0.3 | 0.1 | 0.6 | 0.2 | 20 |
| 2 | 0.5 | 0.4 | 0.7 | 0.6 | 20 |
| 3 | 0.5 | 0.4 | 0.7 | 0.5 | 10 |
| 4 | 0.1 | 0.2 | 0.3 | 0.4 | 10 |
| 5 | 0.7 | 0.4 | 0.6 | 0.4 | 10 |
| 6 | 0.4 | 0.4 | 0.6 | 0.7 | 10 |
| 7 | 7.0 | 9.3 | 11.0 | 13.2 | 4 |
| 8 | — | 3.1 | — | 3.5 | 3 |

*1: free aliphatic monocarboxylic acid, % by weight
*2: free succinic acid or phthalic acid, % by weight Determination of Elongation of Films The sample was dissolved in a 1:1 by volume mixed solvent of methylene chloride and methyl alcohol and films of 0.1 mm thickness were prepared by the casting method with the thus prepared solution. Measurement of elongation was carried out at 25° C.

EXAMPLE 2

A homogeneous, viscous solution was prepared by dissolving 90 g of Sample No. 3 obtained in Example 1 in 210 g of a 6:4 by volume mixed solvent of acetone and ethyl alcohol followed by defoaming by standing at room temperature.

Pin-molds for cap and body of a capsule, treated in advance with a lubricant, were dipped in this solution and pulled up gradually to form a film of the viscous solution therearound followed by drying at 40° to 42° C. into crusts. The thus obtained cap and body of a capsule, taken off from the pin-molds with necessary finishing, were transparent and excellent in pliability.

The capsule was filled with powder of lactose and the coupling portion of the cap and body was sealed with the same viscous solution as above. The solubility behavior of the thus prepared capsules was examined in the first solution with a pH of 1.2 and the second solution with a pH of 7.5 according to the Ninth Revised Japanese Pharmacopoeia as a simulation of gastric juice or intestinal juice, respectively, as well as in McIlvain buffer solutions with pH values of 4.5, 5.0, 5.5 and 6.0 to give results shown in Table 3 below.

TABLE 3

| pH of testing solution | Solubility behavior of capsule |
|---|---|
| 1.2 | Not dissolved for more than 2 hours. |
| 4.5 | Not dissolved for more than 2 hours. |
| 5.0 | Content was released within 20 to 25 minutes out of the dissolved capsule. |
| 5.5 | Content was released within 12 to 15 minutes out of the dissolved capsule. |
| 6.0 | Content was released within 8 to 10 minutes out of the dissolved capsule. |
| 7.5 | Content was released within 6 to 9 minutes out of the dissolved capsule. |

EXAMPLE 3

Experimental procedure was substantially the same as in Example 2 except that the dipping solution was prepared by dissolving 20 g of Sample No. 1 obtained in Example 1 in 80 g of a 8:2 by volume mixed solvent of ethyl alcohol and water. The capsules were also transparent and excellent in pliability. The solubility test undertaken in the same manner as in Example 2 indicated that the capsule was undissolved in the first solution of pH 1.2 for at least 2 hours while dissolved within 15 to 20 minutes in the second solution of pH 7.5 to release the content into the solution.

EXAMPLE 4

Experimental procedure was substantially the same as in Example 2 except that the dipping solution was prepared by dissolving 25 g of Sample No. 5 obtained in Example 1 in 75 g of a 1:1 by volume mixed solvent of acetone and ethyleneglycol monomethyl ether. The capsules were also transparent and excellent in pliability. The solubility test undertaken in the same manner as in Example 2 indicated that the capsule was undissolved in the first solution of pH 1.2 for at least 2 hours while dissolved within 15 to 25 minutes in the second solution of pH 7.5 to release the content into the solution.

EXAMPLE 5

Sample No. 4 obtained in Example 1 was admixed with 5% by weight of polyethyleneglycol having an average molecular weight of about 400 and 0.5% by weight of rice wax in Henschel mixer and the blend was kneaded in a two-roller mill at 130° C. for about 10 minutes and shaped into a sheet of 0.5 mm thickness. This sheet was transparent and excellent in pliability.

The sheet was sandwiched between a male and female metal molds of dimensions and form corresponding to the cap or body of #0 capsule and compression-molded at 120° C. for 3 minutes under a pressure of 40 kg/cm². The thus obtained cap and body of capsule had about 0.2 mm of wall thickness with necessary finishing and was transparent and excellent in pliability.

The capsule was filled with powder of lactose and the coupling portion of the cap and body was sealed with a 15% acetone solution of the same cellulose derivative. The solubility behavior of the thus prepared capsules was examined in the same manner as in Example 2 above with the first and the second solutions according to the Ninth Revised Japanese Pharmacopoeia as well as with McIlvain buffer solutions of pH values 5.0, 5.5 and 6.0 to give the results set out in Table 4 below.

TABLE 4

| pH of testing solution | Solubility behavior of capsule |
|---|---|
| 1.2 | Not dissolved for more than 2 hours. |
| 5.0 | Not dissolved for more than 2 hours. |
| 5.5 | Content was released within 20 to 25 minutes |

TABLE 4-continued

| pH of testing solution | Solubility behavior of capsule |
|---|---|
| | out of the dissolved capsule. |
| 6.0 | Content was released within 10 to 15 minutes out of the dissolved capsule. |
| 7.5 | Content was released within 6 to 9 minutes out of the dissolved capsule. |

EXAMPLE 6

Sample No. 4 obtained in Example 1 was admixed with 5% by weight of propyleneglycol and 2% by weight of stearic acid in a Henschel mixer and the blend was extruded using a single screw extruder of 25 mm diameter at 150° C. with a discharging pressure of 200 kg/cm$^2$ into rods of 2 mm diameter. These rods were chopped in a pelletizing machine into pellets of 5 mm length and the pellets were extruded through a T-die with a 0.2 mm spacer mounted on the same single screw extruder as used above to give films of 0.20 to 0.22 mm thickness having transparency and excellent pliability.

The thus prepared films were shaped into caps and bodies of #0 capsules by the techniques of vacuum forming at 110° C. using respective female metal molds. The wall thickness of the caps and bodies was about 0.1 mm.

The solubility behavior of the capsules was examined in the same manner as in the preceding example to find that the capsule remained undissolved in the first solution of pH 1.2 for more than 2 hours while rapidly dissolved in the second solution of pH 7.5 within 15 to 20 minutes.

EXAMPLE 7

A solution prepared by dissolving 50 g of Sample No. 6 obtained in Example 1 in 450 g of a 1:1 by volume mixed solvent by methylene chloride and methyl alcohol with addition of 5 g of propyleneglycol was spread on a glass plate and dried up to give a film of 0.1 mm thickness.

A simulation tablet prepared with a mixture composed of 59.5% of lactose, 35% of corn starch, 5% of a low-substitution hydroxypropylcellulose and 0.5% of magnesium stearate and having a diameter of 9 mm and weighing 280 mg was sandwiched between two pieces of the above prepared film heated at 120° C. and heat-sealed by pressing the films at the portions just outside the tablet on to the side surface of the tablet to give an enterosoluble encapsulated tablet.

The solubility behavior of the encapsulated tablets was examined in the same manner as in Example with the first and the second solution having pH values of 1.2 and 7.5, respectively, to find that the tablet remained undissolved for more than 2 hours in the first solution while the tablet was dissolved and disintegrated within 8 to 13 minutes in the second solution. The disintegration time of the simulation tablet per se in the second solution was 2.5 to 3.5 minutes.

EXAMPLE 8

A film of 0.1 mm thickness was prepared with Sample No. 2 obtained in Example 1 by the casting method with a 10% solution in a 8:2 by volume mixed solvent of ethyl alcohol and water. An encapsulated tablet was prepared in the same manner as in Example 7 by heat-sealing at 100° C. with the above prepared film. The encapsulated tablet remained undissolved for more than 2 hours in the first solution of pH 1.2 while it was dissolved and disintegrated within 10 to 15 minutes in the second solution of pH 7.5.

What is claimed is:

1. An enterosoluble capsule for containing a medicament shaped with a mixed ester of a cellulose ether substituted with substituent groups selected from the class containing of alkyl groups and hydroxyalkyl groups esterified with acidic succinyl groups and aliphatic monovalent acyl groups wherein the average numbers of substitution of the acidic succinyl groups and the aliphatic monovalent acyl groups bonded to the cellulose ether are at least 0.1 and 0.05, respectively, per glucose unit.

2. The enterosoluble capsule as claimed in claim 1 wherein the average number of substitution of the cellulose ether with alkyl groups is not exceeding 2.5 per glucose unit.

3. The enterosoluble capsule as claimed in claim 1 wherein the aliphatic monovalent acyl group is selected from the class consisting of acetyl, propionyl and butyroyl.

* * * * *